United States Patent [19]
Jones

[11] Patent Number: 5,316,019
[45] Date of Patent: May 31, 1994

[54] CONDOM APPLICATOR

[76] Inventor: Keith G. Jones, Les Cyclades, 37 Avenue Des Papalins, MC 98000 Monaco, Monaco

[21] Appl. No.: 79,979

[22] Filed: Jun. 23, 1993

Related U.S. Application Data

[63] Continuation of Ser. No. 843,320, Feb. 28, 1992, abandoned.

[30] Foreign Application Priority Data

Mar. 5, 1991 [GB] United Kingdom ............... 9104574
Nov. 13, 1991 [GB] United Kingdom ............... 9124058

[51] Int. Cl.⁵ .......................................... A61F 6/04
[52] U.S. Cl. .................................. 128/844; 128/917; 206/69; 604/347
[58] Field of Search ............... 604/349, 346; 128/842, 128/844, 917, 918; 206/69

[56] References Cited

U.S. PATENT DOCUMENTS

| | | |
|---|---|---|
| 4,738,357 | 4/1988 | Martin ................ 604/349 |
| 4,781,288 | 11/1988 | Wing ................... 206/69 |
| 4,784,655 | 11/1988 | Campion ............. 604/349 |
| 4,805,820 | 2/1989 | Kearney .............. 206/69 |
| 4,875,491 | 10/1989 | Parrone .............. 266/69 |
| 4,892,188 | 1/1990 | Meadows ............ 206/69 |
| 4,964,416 | 10/1990 | Foldesy .............. 128/844 |

*Primary Examiner*—Robert A. Hafer
*Assistant Examiner*—David J. Kenealy
*Attorney, Agent, or Firm*—Joseph S. Iandiorio

[57] ABSTRACT

A condom applicator (2) comprising a rolled up condom (4) and a ring member (6) for applying the condom (4) by unrolling it over a penis, the ring member comprising a side wall (8), a flat portion (10), a first lip (12), a second lip (16), and first and second ends (18, 20) which are joined together by a frangible joint (22) which forms the ring member (6) into a complete ring in order to retain the condom (4) in position prior to use of the condom applicator (2) and which breaks during use of the condom applicator (2), and the ring member (6) being constructed to control the tendency of the first and second ends (18, 20) to twist with respect to each other after the frangible joint (22) has been broken.

8 Claims, 3 Drawing Sheets

CONDOM APPLICATOR

This is a continuation of application Ser. No. 07/843320, filed Feb. 28, 1992 abandoned.

This invention relates to a condom applicator.

Condoms have been widely known and used for many years. Many aspects of condoms are disliked by persons using them, including negative spontaneity, general awkwardness in applying the condom, possibly getting the condom inside out, slipperiness of feel, lubricant smell on fingers and cheap, uninspiring packaging.

It is an aim of the present invention to reduce the above mentioned problems, thereby promoting greater user confidence and user ease of application, which in turn encourages the use of the condom in its important function of acting as a contraceptive and helping to prevent the spread of sexually-transmitted diseases.

Accordingly, this invention provides a condom applicator comprising a rolled up condom and a ring member which is of a size such as to hold the rolled up condom in a non-stretched condition and which is for applying the condom by unrolling it over a penis:

the ring member comprising a side wall, a flat portion which extends substantially perpendicularly with respect to the side wall, a first lip which is provided along an inner part of the flat portion and over which the condom runs when it is being applied by the ring member, and a second lip which is spaced apart from the flat portion, which acts with the flat portion to retain the condom in the ring member prior to use and which extends over the rolled up condom by an amount which is less than half the diameter of a rolled up part of the rolled up condom;

the ring member comprising first and second ends which are joined together by an adhesive frangible joint which is located between said ends and which forms the ring member into a complete ring in order to retain the condom in position prior to use of the condom applicator and which breaks during use of the condom applicator in order to allow the ring member to expand radially to accommodate different diameters of penis; and the side wall being constructed to enable the ring member to expand radially to control the tendency of the first and the second ends to twist with respect to each other after the frangible joint has been broken and whilst the ring member is being moved along the penis.

The ring member is advantageous in placing the condom on the penis, ready for rolling on and the right way up. The flat portion enables the condom to unroll smoothly using the current lubricant methods employed on condoms. The first lip helps to stop the ring member from running over the condom roll during unrolling as the ring member is being moved along the penis. The side wall will normally be constructed to give minimum twisting of the first and the second ends of the ring member, whilst permitting maximum opening of the ring member. It will be appreciated that the twisting occurs in one plane whilst the radial opening occurs in a different plane. Since the majority of rolled up condoms are of substantially the same diameter, there is no problem in having the ring member initially in the form of the closed ring. The ring member has to be radially expandable however in order to accommodate different diameters of penis. The wall is thus chosen to be of a shape that permits the radial expansion in a smooth and easy manner. The frangible joint allows easy removal of the ring member after use of the condom applicator when the condom is fully unrolled.

Preferably, the condom applicator is one in which the ring member when closed is minimally larger than the condom. This facilitates compact storing of the condom.

In a first embodiment of the invention, the condom applicator is one in which the side wall is such that the flat portion is positioned substantially halfway along the length of the side wall, and in which the side wall has a forward portion which is thicker than a rearward portion, the forward portion acting to control the tendency of the first and the second ends to twist, by means of its cross section.

In a second embodiment of the invention, the condom applicator is one in which the side wall is such that the flat portion is positioned substantially at a forward end of the side wall, and in which the majority of the side wall is of a uniform cross section, which cross section is chosen to be such as to control the tendency of the first and the second ends to twist.

The condom applicator may be one in which the outer surface of the ring member is provided with grip-increasing means. The grip-increasing means may be radial ribs. If desired however the outer surface of the ring member may be plain.

As stated above, the frangible joint is an adhesive joint. The adhesive should be chosen so that it is not too strong and it breaks relatively easily.

In a third embodiment of the invention, the side wall may be made in two materials of two different strengths, one material being a harder material to control the tendency of the first and the second ends to twist, and the other material being a softer material to allow better radial expansion.

The condom applicator lends itself to being attractively packaged.

The condom applicator may include a primary container, the primary container being such as to house the condom and the ring member.

Usually, the primary container will only contain one condom and one ring member. If desired however, the primary container could contain two or more of the condoms and the ring members.

Preferably, the primary container is a hermetically sealed container, and therefore "germ-free" and untampered.

The primary container may comprise a body portion and a lid. Preferably, the lid is a peel-off lid.

The primary container may include a pull tag for peeling off the lid.

The body portion may be advantageously produced as a vacuum formed tray. Such a tray can be produced to be cheap, small and light. The body portion can also be formed in other ways, for example by injection moulding.

The condom applicator may include a secondary container.

Usually, the secondary container will be for aesthetic purposes, and for giving safe protective carriage in a pocket, handbag or the like.

The secondary container will usually contain two or more of the primary containers. Thus, for example, the secondary container may contain from two to ten of the primary containers, but it may of course contain just one of the primary containers if desired.

Preferably, the secondary container is such that it has a hard inner and a soft outer. Such a secondary container feels and looks different from known containers such for example as powder compact containers.

The hard inner of the secondary container may be made of a plastics material, whilst the soft outer of the secondary container may be made of a rubber material or a foam material.

The secondary container can be constructed such that the soft outer can be pushed in order to eject the primary containers. This is especially advantageous where the primary containers are a relatively tight fit in the secondary containers, to prevent them dropping out accidentally.

The soft outer can be pushed through a hole in the hard inner, in order to push against the primary containers.

The ring member will usually be made of a plastics material. The plastics material will preferably be chosen to give the required qualities of smooth easy radial expansion, whilst controlling the tendency of the first and the second ends of the ring member to twist too much with respect to each other. The plastics material will also be compatible with condom lubricants.

Embodiments of the invention will now be described solely by way of example and with reference to the accompanying drawings in which.

Figure 1:
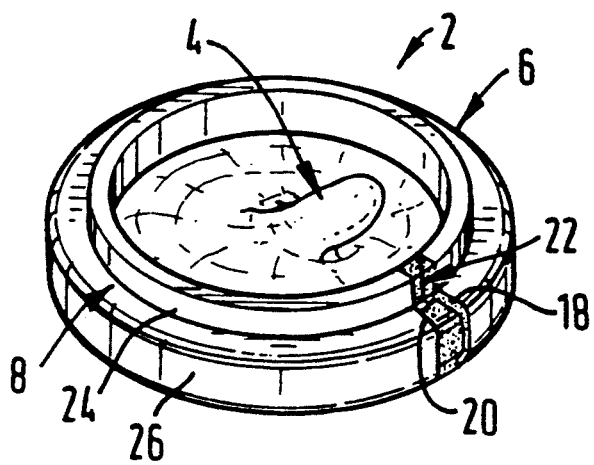
FIG. 1 is a perspective view of a first condom applicator.

Referring to FIG. 1, there is shown a condom applicator 2 comprising a rolled up condom 4 and a ring member 6 for applying a condom 4 over a penis (not shown).

Figure 2:
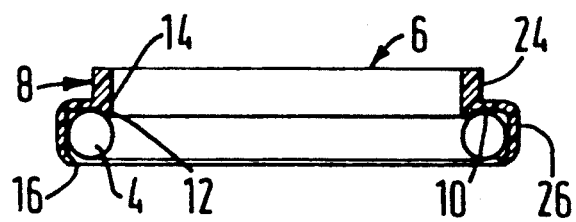
FIG. 2 is a cross section through the condom applicator shown in FIG. 1.

The ring member 6 comprises a side wall 8 and a flat portion 10 which extends substantially perpendicularly to the side wall 8 as can be seen from FIG. 2.

The ring member 6 also comprises a first lip 12 which is provided along an inner part 14 of the flat portion 10. The condom 4 runs over this first lip 12 when the condom 4 is being applied over a penis by the ring member 6.

The ring member 6 also includes a second lip 16 which is spaced apart from the flat portion 10 as shown and which acts with the flat portion 10 to retain the rolled up condom 4 in the ring member 6 during lifting and placing on to the penis.

The ring member 6 comprises a first end 18 and a second end 20. The first and the second ends 18,20 are joined together by a frangible joint in the form of an adhesive joint 22. The adhesive joint 22 forms the ring member 6 into a complete ring. This is so as to retain the condom 4 in position prior to use of the condom applicator 2. The adhesive joint 22 breaks during use of the condom applicator 2 in order to allow the ring member 6 to expand radially to accommodate different diameters of penis.

The side wall 8 has a portion 24 which is constructed to control the tendency of the first and the second ends to twist with respect to each other after the adhesive joint 22 has been broken and whilst the ring member 6 is being moved along the penis.

As can be seen from FIGS. 1 and 2, when the ring member 6 is in its closed position, then the ring member 6 is only slightly larger than the condom 4. Thus the ring member 6 does not occupy too much space which is advantageous for packaging purposes.

The cross sectional shape of the flat portion 10 as shown in FIG. 2 is advantageous in permitting the easy and smooth radial expansion of the ring member 6. As can be seen from FIG. 2, the side wall 8 is such that the flat portion 10 is positioned substantially halfway along the length of the side wall 8. The side wall 8 has a portion 26 which is thinner that the portion 24. The portion 26 acts with the flat portion 10 to retain the condom 4.

Figure 3:
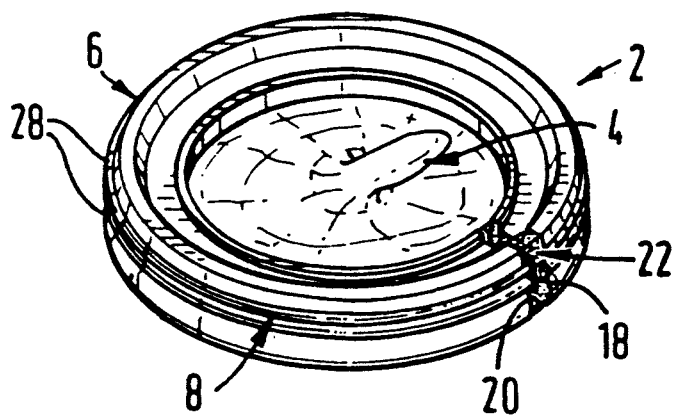
FIG. 3 is a perspective view of a second condom applicator.
Figure 4:
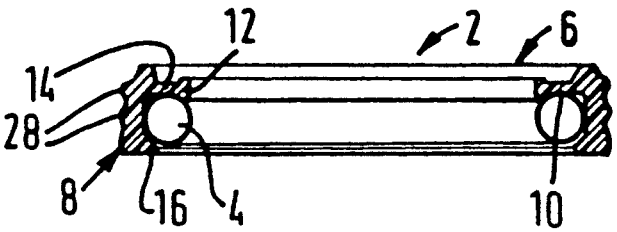
FIG. 4 is a cross section through the condom applicator shown in FIG. 3.

Referring now to FIGS. 3 and 4, there is shown a second condom applicator 2 in which similar parts as in FIGS. 1 and 2 have been given the same reference numerals for ease of comparison and understanding. In FIGS. 3 and 4 it will be seen that the side wall 8 is such that the flat portion 10 is positioned substantially at a forward end of the side wall 8.

The height of the side wall 8 is chosen to be such as to control the tendency of the first and the second ends 18, 20 to twist with respect to each other.

As can be seen from FIGS. 3 and 4, the outer surface of the ring member 6 is provided with grip-increasing means in the form of radial ribs 28.

Figure 5:
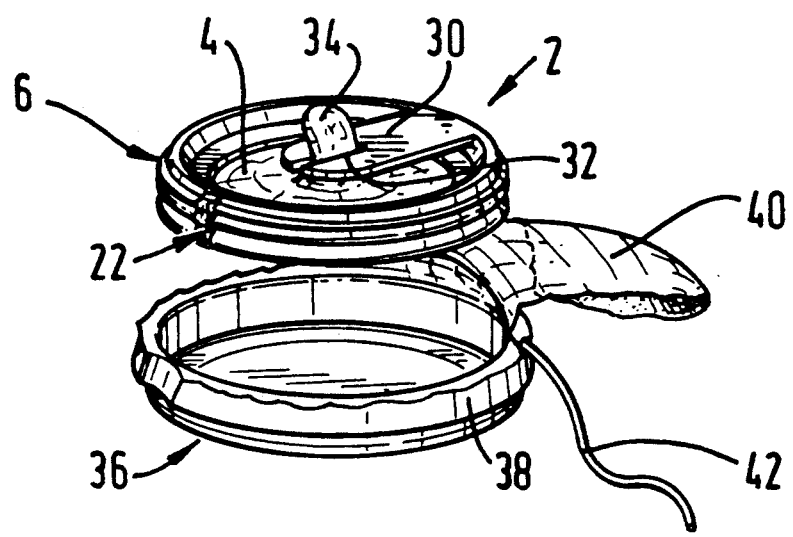
FIG. 5 is a perspective view of a condom applicator having a primary pack with a peel-off lid and pull tag.

FIG. 5 shows a condom applicator 2 comprising a condom 4 and a ring member 6. The ring member 6 has a radially inwardly projecting arm 30. The arm 30 is provided with a slit 32 for accommodating a teat part 34 of the condom 4. The slit 32 acts to keep the teat part 34 squeezed closed which helps to prevent the ingress of air into the teat part 34 during use of the condom applicator 2.

FIG. 5 shows the condom 4 and the ring member 6 in the form of a pack being inserted into a primary container 36. The primary container 36 is a sealed container.

The primary container 36 comprises a body portion 38 and a lid 40. The lid 40 is a peel-off lid. The primary container 36 includes a pull tag 42 for peeling off the lid 40. As shown, the pull tag 42 goes around a top circumferential part of the body portion 38.

Figure 6:
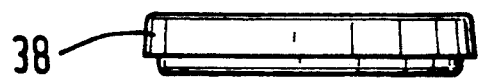
FIG. 6 is a side view of the primary pack.
Figure 7:
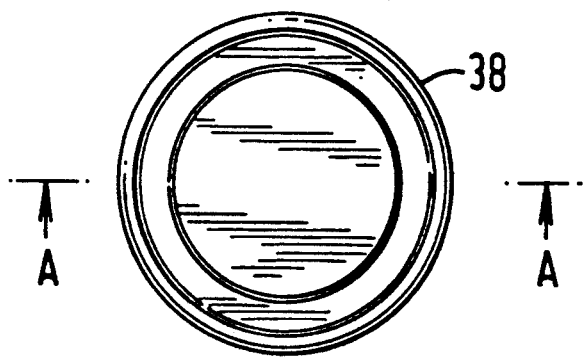
FIG. 7 is a plan view of the primary pack.
Figure 8:
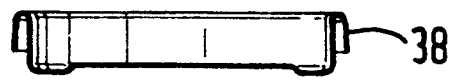
FIG. 8 is a cross sectional view on the line A—A shown in FIG. 7.

FIGS. 6, 7 and 8 show the shape of the body portion 38. The body portion 38 is a vacuum formed body portion 38 which can thus be produced of the minimum of material and to be very light.

Figure 9:
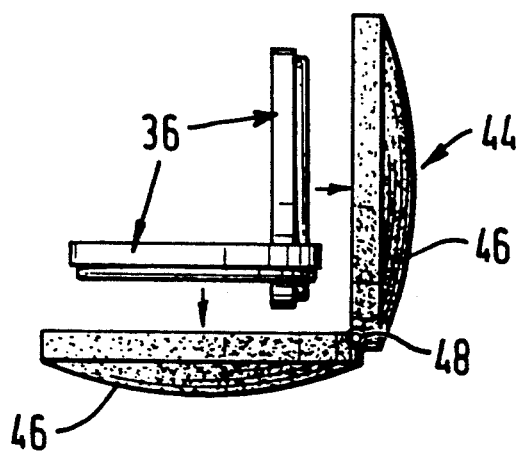
FIG. 9 shows primary and secondary containers forming part of a condom applicator.

FIG. 9 shows two of the primary containers 36 being inserted into a secondary container 44.

Figure 10:
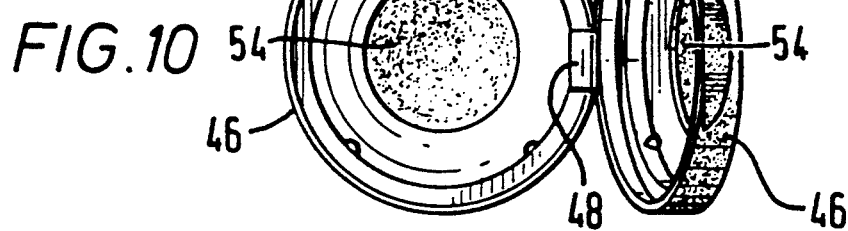
FIG. 10 shows in detail the secondary container shown in FIG. 9.
Figure 11:
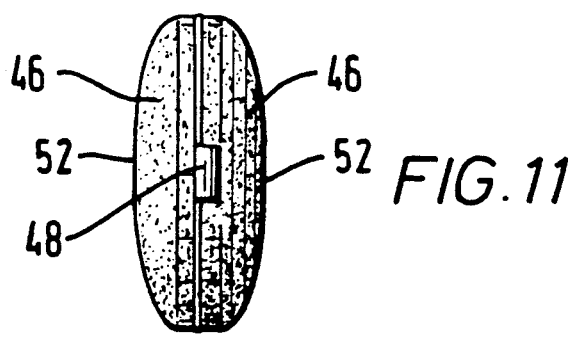
FIG. 11 shows the secondary container of FIG. 10 closed.
Figure 12:
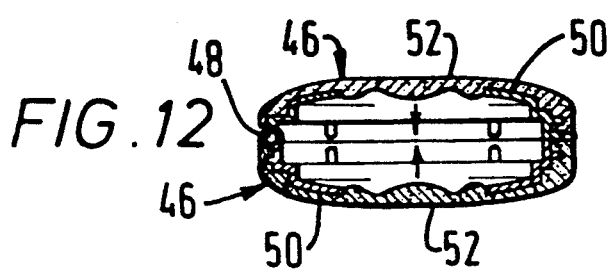
FIG. 12 is a cross section through the secondary container shown in FIG. 10.

The secondary container 44 has two similar parts 46 which are hinged together by a hinge 48. The precise construction of the secondary container 44 is shown more clearly in FIGS. 10, 11 and 12. A clip is provided to shut the secondary container 44 tightly.

Each part 46 of the secondary container 44 has a hard inner 50 and a soft outer 52. The hard inner 50 has a hole 54 and the soft outer 52 can be pushed slightly through this hole 54. The pushing of the soft outer 52 through the hole 54 is effective to push one of the primary containers 36 out of its part 46 of the secondary container 44. Thus the primary containers 36 can be securely housed in the secondary container 44, whilst at the same time being easily obtainable from the secondary container 44.

It is to be appreciated that the embodiments of the invention described above with reference to the accompanying drawings have been given by way of example only and that modifications may be effected. Thus, for example, referring to FIG. 2, the portion 24 could be made of a relatively hard material in order to control the tendency of the first and the second ends 18, 20 to twist with respect to each other, whilst the flat portion 10 and the portion 26 could be made of a softer material. Also, different types of cross sectional constructions may be employed for the ring member 6. Still further, different types of primary containers 36 and secondary containers 44 may be employed.

I claim:

1. A condom applicator comprising a rolled up condom and a ring member which is of a size such as to hold the rolled up condom in a non-stretched condition and which is for applying the condom by unrolling it over a penis:

the ring member comprising a side wall, a flat portion which extends inwardly from the side wall and substantially perpendicularly with respect to the side wall, a first lip which is provided along an inner part of the flat portion and over which the condom runs when it is being applied by the ring member, and a second lip which extends inwardly from the side wall at a position remote from where the flat portion extends from the side wall, which acts with the flat portion to define a recess and to retain the condom in the recess prior to use, and which extends over the rolled up condom by an amount which is less than half the diameter of a rolled up part of the rolled up condom;

the ring member being a single moulded component comprising first and second ends which are joined together by a frangible joint formed by an adhesive which is located between said ends and which forms the ring member into a complete ring in order to retain the condom in position prior to use of the condom applicator and which breaks during use of the condom applicator in order to allow the ring member to expand radially to accommodate different diameters of penis; and the side wall being constructed to enable the ring member to expand radially and to control the tendency of the first and the second ends to twist with respect to each other after the frangible joint has been broken and whilst the ring member is being moved along the penis.

2. A condom applicator according to claim 1 in which the side wall is such that the flat portion is positioned substantially halfway along the length of the side wall, in which the side wall has a forward portion which is thicker than a rearward portion, the forward portion acting to control the tendency of the first and the second ends to twist by means of its cross section, and in which the outer surface of the ring member is provided with grip-increasing circular ribs.

3. A condom applicator according to claim 1 in which the side wall is such that the flat portion is positioned substantially at a forward end of the side wall, in which the majority of the side wall is of a uniform cross section, which cross section is chosen to be such as to control the tendency of the first and the second ends to twist, and in which the outer surface of the ring member is provided with grip-increasing circular ribs.

4. A condom applicator according to claim 1 and including a primary container, the primary container being such as to house the condom and the ring member.

5. A condom applicator according to claim 4 in which the primary container is a hermetically sealed container, in which the primary container comprises a body portion and a lid, and in which the lid is a peel-off lid.

6. A condom applicator according to claim 4 and including a secondary container for containing the primary container.

7. A condom applicator according to claim 4 in which the secondary container is such that it has a hard inner and a soft outer, and in which the soft outer is such that it can be pushed through a hole in the hard inner in order to push against the primary container and eject the primary container from the second container.

8. A condom applicator comprising a rolled up condom and a ring member which is of a size such as to hold the rolled up condom in a non-stretched condition and which is for applying the condom by unrolling it over a penis:

the ring member comprising a side wall, a flat portion which extends inwardly from the side wall and substantially perpendicularly with respect to the side wall, a first lip which is provided along an inner part of the flat portion and over which the condom runs when it is being applied by the ring member, and a second lip which extends inwardly from the side wall at a position remote from where the flat portion extends from the side wall, which acts with the flat portion to define a recess and to retain the condom in the recess prior to use, and which extends over the rolled up condom by an amount which is less than half the diameter of a rolled up part of the rolled up condom;

the ring member being a single moulded component comprising first and second ends which are joined together by a frangible joint formed by an adhesive which is located between said ends and which forms the ring member into a complete ring in order to retain the condom in position prior to use of the condom applicator and which breaks during use of the condom applicator in order to allow the ring member to expand radially to accommodate different diameters of penis;

the side wall being constructed to enable the ring member to expand radially and to control the tendency of the first and the second ends to twist with respect to each other after the frangible joint has been broken and whilst the ring member is being moved along the penis; and the condom applicator being one in which the side wall comprises a forward portion which is made of a first material and a rearward portion which is made of a second material, the first material being harder material to control the tendency of the first and the second ends to twist, and the second material being a softer material to allow better radial expansion.

* * * * *